(12) United States Patent
Uraoka et al.

(10) Patent No.: US 11,559,602 B2
(45) Date of Patent: Jan. 24, 2023

(54) SOL FOR TISSUE PERFORATION CLOSURE, ULCER PROTECTION, AND VASCULAR EMBOLIZATION

(71) Applicants: Tokyo Metropolitan Industrial Technology Research Institute, Tokyo (JP); National University Corporation Gunma University, Gunma (JP)

(72) Inventors: Toshio Uraoka, Tokyo (JP); Naohisa Yahagi, Tokyo (JP); Shunji Yunoki, Tokyo (JP); Yoshimi Ohyabu, Tokyo (JP); Takefumi Narita, Tokyo (JP)

(73) Assignees: Tokyo Metropolitan Industrial Technology Research Institute, Tokyo (JP); National University Corporation Gunma University, Gunma (JP)

( * ) Notice: Subject to any disclaimer, the term of this patent is extended or adjusted under 35 U.S.C. 154(b) by 0 days.

(21) Appl. No.: 16/461,527

(22) PCT Filed: Nov. 16, 2017

(86) PCT No.: PCT/JP2017/041238
§ 371 (c)(1),
(2) Date: May 16, 2019

(87) PCT Pub. No.: WO2018/092836
PCT Pub. Date: May 24, 2018

(65) Prior Publication Data
US 2019/0343992 A1 Nov. 14, 2019

(30) Foreign Application Priority Data
Nov. 17, 2016 (JP) .............................. JP2016-224255

(51) Int. Cl.
| | | |
|---|---|---|
| A61L 24/10 | (2006.01) | |
| A61K 9/00 | (2006.01) | |
| A61K 47/02 | (2006.01) | |
| A61K 47/22 | (2006.01) | |
| A61K 47/42 | (2017.01) | |
| A61L 31/14 | (2006.01) | |
| A61K 9/06 | (2006.01) | |
| A61L 27/24 | (2006.01) | |
| A61L 31/04 | (2006.01) | |

(52) U.S. Cl.
CPC .......... *A61L 24/102* (2013.01); *A61K 9/0019* (2013.01); *A61K 47/02* (2013.01); *A61K 47/22* (2013.01); *A61K 47/42* (2013.01); *A61L 31/14* (2013.01); *A61F 2310/00365* (2013.01); *A61K 9/06* (2013.01); *A61L 24/104* (2013.01); *A61L 27/24* (2013.01); *A61L 31/04* (2013.01); *A61L 2300/418* (2013.01); *A61L 2400/04* (2013.01); *A61L 2400/06* (2013.01); *A61L 2430/36* (2013.01)

(58) Field of Classification Search
None
See application file for complete search history.

(56) References Cited

U.S. PATENT DOCUMENTS

| | | | | |
|---|---|---|---|---|
| 4,708,718 A | * | 11/1987 | Daniels | .................. C07K 14/78 |
| | | | | 128/DIG. 8 |
| 8,226,971 B2 | * | 7/2012 | Ash | ........................ A01N 37/04 |
| | | | | 424/423 |
| 2006/0239958 A1 | | 10/2006 | Taguchi et al. | |
| 2010/0240750 A1 | | 9/2010 | Ash | |
| 2011/0201541 A1 | | 8/2011 | Takamura et al. | |
| 2016/0000966 A1 | | 1/2016 | Kobayashi et al. | |
| 2020/0040030 A1 | * | 2/2020 | Wang | .................. A61L 27/3612 |

FOREIGN PATENT DOCUMENTS

| | | | | |
|---|---|---|---|---|
| CN | 104689381 A | 6/2015 | | |
| JP | 1988500566 A | 3/1988 | | |
| JP | 4585743 B | 9/2004 | | |
| JP | 2007325824 A | 12/2007 | | |
| JP | 2008505919 A | 2/2008 | | |
| JP | 5019851 B | 5/2008 | | |
| JP | 2014103985 A | 6/2014 | | |
| JP | 2014221830 A | 11/2014 | | |
| JP | 2016077410 A | 5/2016 | | |
| JP | 2016515113 A | 5/2016 | | |
| WO | 1987000062 A | 1/1987 | | |
| WO | WO-9213578 A1 | * | 8/1992 | ........... A61L 24/043 |
| WO | 2000045868 A | 8/2000 | | |
| WO | 2006014570 A | 2/2006 | | |
| WO | 2006116524 A | 11/2006 | | |

(Continued)

OTHER PUBLICATIONS

Machine-assisted English translation for JP 2016-77410 (Year: 2016).*
Machine-assisted English translation for JP 2014103985 A (Year: 2014).*
International Search Report received in PCT/JP2017/041238 dated Jan. 23, 2018.
Written Opinion received in PCT/JP2017/041238 dated Jan. 23, 2018.

(Continued)

*Primary Examiner* — Sin J Lee
(74) *Attorney, Agent, or Firm* — Suzannah K. Sundby, Esq.; Canady + Lortz LLP

(57) ABSTRACT

The purpose of the present invention is to provide an injectable sol into a body, suited for delivery through a catheter, and usable for tissue perforation closure, ulcer protection, or vascular embolization. Provided are a sol for tissue perforation closure, a sol for ulcer protection, and a sol for vascular embolization, each containing from 0.6 mass % to 3 mass % of a collagen, water, from 200 mM to 330 mM sodium chloride, and a buffer and having a pH from 6.0 to 9.0.

20 Claims, 9 Drawing Sheets

(56) References Cited

FOREIGN PATENT DOCUMENTS

| WO | 2007087350 A | 8/2007 |
|----|--------------|--------|
| WO | 2010041636 A | 4/2010 |

OTHER PUBLICATIONS

Narita et al, "In situ gelation properties of a collagengenipin sol with a potential for the treatment of gastrointestinal ulcers", Dec. 15, 2016, pp. 429-439, vol. 2016, No. 9, Publisher: Medical Devices: Evidence and Research.

Tsuji et al., "Endoscopic tissue shielding method with polyglycolic acid sheets and fibrin glue to cover wounds after colorectal endoscopic submucosal dissection . . . ", Oct. 21, 2013, pp. 151-155, vol. 79, No. 1, Publisher: Gastrointestinal Endoscopy.

Yunoki et al., "A novel fabrication method to create a thick collagen bundle composed of uniaxially aligned fibrils: An essential technology for the development of . . . ", Feb. 26, 2015, pp. 3054-3065, vol. 103A, Publisher: J Biomed Mater Res Part A.

Yunoki et al., "This abstract describes in vivo experiments as disclosed in JP2016-224255 which is the same as PCT/JP2017/041238", "Properties required for using injectable gel for countermeasure against accident in endoscopic therapy for digestive organs for Biomaterials", Nov. 21, 2016, p. 195 (abstract), No. 2C-06, Publisher: Symposium 2016 of The Japanese Society.

Database WPI, Week 201638, Thomson Scientific, London, GB; AN 2016-29485U, XP002799692, & JP2016077411 A(Tokyo Metropolitan Indtechnology Res In) May 16, 2016 (May 16, 2016).

Database WPI, Week 201636, Thomson Scientific, London, GB; AN 2016-294887, XP002799693, & JP2016077410 A(Tokyo Metropolitan Ind Technology Res In) May 16, 2016 (May 16, 2016).

Database EPODOC [Online], European Patent Office, Thehague, NL; XP002799694, Database accession No. CN-201310671193-A; & CN 104689381 A (Univfudan) Jun. 10, 2015 (Jun. 10, 2015).

Takao H, Murayama Y, Ebara M, et al. New thermoreversible liquid embolic agent for embolotherapy: technical report. Neuroradiology. 2009;51(2):95-98.

* cited by examiner

SOL FOR TISSUE PERFORATION CLOSURE, ULCER PROTECTION, AND VASCULAR EMBOLIZATION

TECHNICAL FIELD

The present invention relates to an injectable sol into a body which is useful for endoscopic treatment or the like. More specifically, it relates to a sol for tissue perforation closure, ulcer protection, and vascular embolization used for the purpose of closing a perforation formed during endoscopic treatment or the like, protecting an ulcer which may occur during endoscopic treatment or the like, or carrying out vascular embolization and thereby stopping the bleeding in cancer treatment or gastrointestinal hemorrhage.

BACKGROUND ART

Minimally invasive treatments such as endoscopic treatment and IVR (interventional radiology) treatment (treatment by inserting a catheter into the living body while using an image diagnostic apparatus with X ray, CT or the like) have been spreading rapidly. These minimally invasive treatments are sometimes required to use an injectable gel into a body for closing a through-hole which has appeared in the tissue, protecting an ulcer, or embolizing a blood vessel. Delivery of a medicinal solution or material through a catheter is important for the minimally invasive treatments, but delivery of a solid material through a catheter is not so easy.

As clinically used preparations having gelation ability, there are preparations making use of a reaction between a crosslinking agent and a polymer and preparations making use of a polymerization reaction of a monomer, each called "bio-adhesive" (also called bio-sealant or tissue adhesive) (Patent Document 1, etc.). They have a function of forming gel and binding to the tissue in a short time, but are unsuited when used for the delivery through a long thin tube such as catheter, because they start gelation immediately after their components are mixed. They have therefore difficulty in use for tissue perforation closure, ulcer protection, and vascular embolization which are often performed endoscopically.

There is also a report on an injectable gel into a body which causes sol-gel transfer by the self-organization (hydrophobic interaction, electrostatic interaction, or the like) of a polymer without using a crosslinking agent (Patent Documents 2 to 4, etc.). It has an advantage such as easy delivery, for example, through a catheter because gelation occurs in response to the body temperature. It is however weak, instable and inferior in fixation to the tissue, making it difficult to use it for tissue perforation closure, ulcer protection, and vascular embolization.

Further, as a preparation used generally as a biosealant or hemostat, there is a fibrin glue making use of a fibrinogen-thrombin crosslinking reaction which is one of bioreactions. Although it can be delivered through a catheter due to a long gelation time after mixing of a medicinal solution and has a hemostatic effect, it has difficulty in locally forming a gel with good reproducibility because gelation of it does not occur in response to the body temperature. Even if a gel is locally formed, it does not have sufficient strength so that an ulcer cannot be shielded stably therewith without combined use of a protective sheet such as polyglycolic acid sheet (Non-Patent Document 1). Due to markedly low adhesion to the tissue (Patent Document 5), the gel lacks stability as a material for closure, embolization/occlusion, or protection. Further, it is one of the blood preparations and as can be seen from a report on infection with hepatitis C or the like, using it may be risky from the viewpoint of safety.

On the other hand, the present inventors have already found that a specific aqueous collagen/genipin mixed solution has gelation properties in which conversion of a collagen into collagen fibrils at a temperature near the body temperature is followed by introduction of genipin crosslinking (Patent Document 6). The present inventors have also found that adjustment of the concentration of an inorganic salt can increase the gelation rate of a specific aqueous collagen solution (Patent Document 7 and Non-Patent Document 2). Effectiveness of these aqueous solutions to a particular medical use has however not yet been known.

CITATION LIST

Patent Documents

Patent Document 1: JP 4585743 B
Patent Document 2: JP 5019851 B
Patent Document 3: JP 2008-505919 T
Patent Document 4: JP 2014-221830 A
Patent Document 5: JP 2007-325824 A
Patent Document 6: JP 2014-103985 A
Patent Document 7: JP2016-077410 A

Non-Patent Document

Non-Patent Document 1: Tsuji et al. Gastrointestinal Endoscopy Volume 79, Issue 1, Pages 151-155, 2014
Non-Patent Document 2: Yunoki et al. Journal of Biomedical Materials Research Part A Volume 103, Issue 9, pages 3054-3065, 2015

SUMMARY

Problem to be Solved

As described above, an injectable gel into a body usable for the tissue perforation closure, ulcer protection, or vascular embolization and suited for delivery through a catheter has not been known. In addition, there have been no examples of delivering a substance in sol form through a catheter and succeeding in tissue perforation closure, ulcer protection or vascular embolization with a gel obtained by sol-gel transfer.

In such a background, an object of the present invention is to provide an injectable sol into a body which can be used for the tissue perforation closure, ulcer protection, or vascular embolization and is suited for delivery through a catheter.

With a view to achieving the above-described object, the present inventors have found that a sol containing a specific concentration of collagen, water, a specific concentration of sodium chloride, and a buffer and having a specific pH has following three properties suited for closure of a through-hole, physical protection of an ulcer, and vascular embolization, that is, (1) long fluidity retention time permitting delivery to the living body, from outside to inside, through a catheter (2) a sharp response to the body temperature to form gel promptly after delivery, and (3) a property of curing after gelation and fixing to the tissue so that using it can achieve tissue perforation closure, ulcer protection, or vascular embolization, and thereby completed the present invention.

The present invention relates to the followings:

[1] A sol for tissue perforation closure, containing from 0.6 mass % to 3 mass % of a collagen, water, from 200 mM to 330 mM sodium chloride, and a buffer and having a pH from 6.0 to 9.0.

[2] A sol for ulcer protection, containing from 0.6 mass % to 3 mass % of a collagen, water, from 200 mM to 330 mM sodium chloride, and a buffer and having a pH from 6.0 to 9.0.

[3] A sol for vascular embolization, containing from 0.6 mass % to 3 mass % of a collagen, water, from 200 mM to 330 mM sodium chloride, and a buffer and having a pH from 6.0 to 9.0.

[4] The sol as described in any of [1] to [3], wherein the buffer contains a phosphate.

[5] The sol as described in any of [1] to [4], containing from 40 mg/L to 1400 mg/L of genipin or a genipin derivative.

[6] The sol as described in any of [1] to [5], wherein the collagen includes a telopeptide-removed collagen.

[7] The sol as described in any of [1] to [6], containing from 1.4 mass % to 1.7 mass % of the collagen and locally delivered to a tissue through a catheter.

[8] The sol as described in any of [1] to [7], which forms gel and attaches to a tissue when brought into contact with the tissue.

The present invention also relates to the followings:

[9] A kit for performing tissue perforation closure, ulcer protection, or vascular embolization with a sol that forms gel and attaches to a tissue when brought into contact with the tissue, comprising a collagen, sodium chloride, a buffer, and genipin for forming the sol.

[10] A kit for performing tissue perforation closure, ulcer protection, or vascular embolization with a sol that forms gel and attaches to a tissue when brought into contact with the tissue, comprising:

a sol comprising from 0.6 mass % to 3 mass % of a collagen, water, from 200 mM to 330 mM sodium chloride, and a buffer and having a pH from 6.0 to 9.0; and genipin.

[11] A tissue perforation closure method using the sol as described in any of [1] to [8].

[12] An ulcer protection method using the sol as described in any of [1] to [8].

[13] A vascular embolization method using the sol as described in any of [1] to [8].

Effects of the Invention

The present invention makes it possible to perform closure of a through-hole of the tissue, protection of an ulcer, or vascular embolization with a sol deliverable through a catheter.

BRIEF DESCRIPTION OF THE DRAWINGS

FIG. 8a shows the evaluation results of the response of gelation to body temperature and FIG. 8b shows the tracing results of G' until 30 minutes after preparation of the sol.

FIG. 9a shows the respective gelation behaviors of the sols different in NPB concentration and FIG. 9b shows the results of plotting the gelation time after the temperature reaches 37° C. with respect to the NPB concentration.

FIG. 10a shows a stress-strain curve and FIG. 10b shows a modulus of elasticity, each of gels different in genipin concentration.

DESCRIPTION OF EMBODIMENTS

Figure 1:
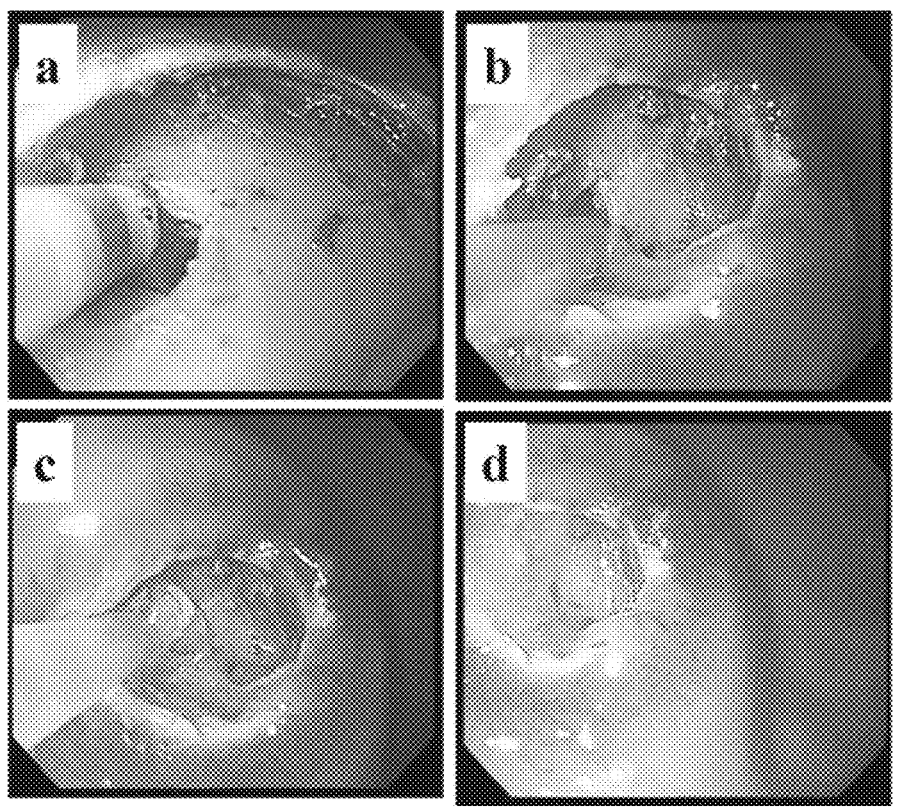
FIG. 1 shows, in a in vivo experiments for closing tissue perforation of porcine stomachs in Test 1, perforation in a porcine stomach (FIG. 1a), delivery of a collagen sol (FIG. 1b), gelation (FIG. 1c), and perforation closure (FIG. 1d).

An embodiment for carrying out the invention (which may hereinafter be called "present embodiment", simply) will hereinafter be described in detail. The present embodiment described below is an example for describing the present invention and does not intend to limit the present invention only to the present embodiment.

The sol (sol composition, pharmaceutical composition) of the present embodiment contains from 0.6 mass % to 3 mass % of a collagen, water, from 200 mM to 330 mM sodium chloride and a buffer and has a pH from 6.0 to 9.0.

Although the collagen contained in the sol of the present embodiment is not particularly limited, it is preferably a telopeptide-removed collagen hard to proceed with fibril formation near the room temperature and it is more preferably composed substantially of the telopeptide-removed collagen. The telopeptide-removed collagen is obtained by enzymatically degrading and removing a telopeptide present at both ends of the collagen molecule by a proteolytic enzyme. For example, it is obtained by degrading and removing a telopeptide present at both ends of the collagen molecule by pepsin digestion. Of telopeptide-removed collagens, telopeptide-removed collagens derived from mammals approved as a raw material for a medical apparatus are preferred, with telopeptide-removed collagens obtained from the porcine dermis, already used clinically, and excellent in thermal stability being more preferred. Telopeptide-removed collagens are commercially available as an alternate name, that is, atelocollagen and they are easily available.

Collagens are not particularly limited insofar as they are collagens having fibril forming ability (fibril-forming collagens). Of the fibril-forming collagens, a Type I collagen constituting the bone, skin, tendon and ligament, a Type II collagen constituting the cartilage, and a Type III collagen contained in the tissue composed of the Type I collagen are preferably used from the viewpoint of their availability, plentiful research results or similarly to the tissue to which the prepared gel is applied. The collagen may be obtained by extraction·purification from the tissue by the conventional method or it may be a commercially available one. The collagen may be a purified product of any of the above-described types or a mixture of a plurality of the above-described types.

The denaturation temperature of the collagen is preferably 32° C. or more, more preferably 35° C. or more, further more preferably 37° C. or more. At the denaturation temperature of 32° C. or more, the fluidity of the sol at room temperature can be kept for a longer period of time and at the same time, in vivo denaturation of the collagen is suppressed. The upper limit of the denaturation temperature of the collagen is not particularly limited, but it is preferably 50° C. or less, more preferably 45° C. or less, still more preferably 41° C. or less. The denaturation temperatures not more than the above-described upper limit can allow the gelation at the time when the sol is brought into contact with the tissue to proceed more promptly. The denaturation temperature of the collagen is measured by the conventional method based on a change in circular dichroism, optical rotation, or a viscosity with an increase in the temperature of an aqueous collagen solution. The denaturation temperature of the collagen may be adjusted by selecting a collagen having a denaturation temperature within the above-described value range.

The sol of the present embodiment contains an aqueous collagen solution containing a collagen and water. From the viewpoint of sol retentivity for locally forming gel at a delivered site, a sol having a high collagen concentration is preferred. The sol having a too low collagen concentration has a reduced viscosity and the sol may dissipate from the introduced site before gelation. In addition, a gel obtained from the sol having a higher collagen concentration has improved hardness so that from the viewpoint of reliably achieving tissue through-hole closure, vascular embolization, or the like, a sol having a high collagen concentration is desired.

On the other hand, from the viewpoint of delivering the sol of the present embodiment through a catheter, the sol has preferably a low collagen concentration. With an increase in the collagen concentration, the sol has a higher viscosity and has increased extrusion resistance, making it difficult to deliver it, though depending on the diameter or length of the catheter.

From the above-described viewpoints, the concentration of the collagen in the sol of the present embodiment is from 0.6 mass % to 3.0 mass %, preferably from 0.8 mass % to 2.2 mass %, more preferably from 1.4 mass % to 1.7 mass %, particularly preferably from 1.4 mass % to 1.6 mass %, each based on the total amount of the sol.

Since the sol of the present embodiment contains a predetermined concentration of sodium chloride which is an inorganic salt, fibril formation of the collagen is accelerated at the time when the sol is brought into contact with the tissue and the sol forms gel promptly in response to the body temperature.

The concentration of sodium chloride contained in the sol can be adjusted as needed to fall within a range of from 200 mM to 330 mM that is higher than a physiological salt concentration (140 mM). The concentration is preferably from 220 mM to 310 mM and it can be adjusted to, for example, around 280 mM. When the concentration of sodium chloride is less than the physiological salt concentration, it sometimes takes long time for collagen fibril formation in response to the body temperature. When the concentration of sodium chloride exceeds 330 mM, on the other hand, the sol may easily lose its fluidity in the catheter. Adjustment of the concentration of sodium chloride to fall within the above-described range makes it possible to form gel promptly in response to the body temperature while maintaining the fluidity of the sol in the catheter.

The sol of the present embodiment has a pH (pH at 23° C., which equally applies to that described herein unless otherwise particularly specified) of from 6.0 to 9.0, more preferably from 6.5 to 8.0. The fibril formation of a collagen is known to vigorously occur near neutral. By adjusting the pH to fall within the predetermined range, fibril formation of a collagen can be accelerated more. The pH can be adjusted by the conventional method, for example, by adjusting the concentration of an inorganic salt contained in the sol, preferably the concentration of sodium chloride and sodium hydrogen phosphate or by adding a strong acid and/or a strong alkali such as hydrochloric acid or sodium hydroxide. The pH can be measured by a known pH meter (for example, "NAVIh F-71", trade name; product of HORIBA).

The sol of the present embodiment contains a buffer for maintaining its pH or the like. Although the buffer is not particularly limited insofar as the sol has desired properties, examples include phosphates, acetates, borates, HEPES and Tris. As the phosphates, sodium phosphate, sodium hydrogen phosphate (collective term for sodium dihydrogen phosphate and disodium hydrogen phosphate), potassium hydrogen phosphate (collective term for potassium dihydrogen phosphate and dipotassium hydrogen phosphate) and the like can be used. As the acetates, sodium acetate and the like can be used, while as the borates, sodium borate and the like can be used. They can each be used in combination with sodium hydroxide or the like serving for pH adjustment. Alternatively, a buffer solution such as a sodium chloride-containing phosphate buffer solution (NPB) using the above-described sodium chloride and buffer in combination may be used.

Of these buffers, phosphates and NPB having a phosphate therein are particularly preferred. The phosphates have such advantages that they are excellent in buffering ability at pH from 6 to 9 at which fibril formation of a collagen occurs vigorously and their safety to living bodies has been confirmed as can be understood from that they are contained in a cell washing solution such as phosphate buffered saline.

The concentration of the buffer is not particularly limited insofar as the pH is kept within a desired range and the sol has desired properties.

From the viewpoint of allowing the buffer to exhibit a pH buffering effect sufficiently, the concentration of the buffer can be adjusted to 5 mM or more. When the concentration of the buffer becomes too high, the salt in the buffer solution may precipitate before preparation of a sol or excessive increase in the ionic strength may bring about histological damages upon use of the sol. The concentration of the buffer can therefore be adjusted to 140 mM or less. The concentration of the buffer is preferably more than 10 mM to less than 120 mM, for example, from 20 mM to 110 mM. The concentration is more preferably from 30 mM to 100 mM. Adjustment of the concentration of the buffer to fall within the above-described range facilitates maintenance of the pH of the sol within a range of from 6.0 to 9.0, making it possible to allow the sol to exhibit the effect of the sol of the present embodiment, that is, retention of the fluidity of the sol in a catheter and after delivery through the catheter, gelation at the delivered site promptly in response to the body temperature; and at the same time, making it possible to suppress precipitation of a salt or histological damages.

When the sol comes into contact with the tissue, it forms gel, responding to the body temperature. In order to enhance the strength of the gel and enhance the attachment to the tissue, the above-described sol may contain a crosslinking agent. The crosslinking agent is not particularly limited and one agent may be used alone or two or more agents may be used in combination. Genipin derived from a plant and said to have low cytotoxicity, which is a crosslinking agent itself, 1-(3-dimethylaminopropyl)-3-ethyl carbodiimide (which will hereinafter be called "EDC"), as a crosslinking agent, to be washed off with water because it is not inserted between collagen molecules, N-hydroxysuccinimide (NHS) as a crosslinking aid thereof, and the like are preferred. Genipin is aglycone derived from geniposide. It can be obtained, for example, by oxidation, reduction and hydrolysis of geniposide or by enzymatic hydrolysis of geniposide. Geniposide is an iridoid glycoside contained in *gardenia* of the family Rubiaceae and is extracted from the *gardenia*. Genipin is represented by the molecular formula of $C_{11}H_{14}O_5$. It may be obtained by synthesis by the conventional method or a commercially available product may be used. Genipin may be derivatized insofar as derivatization does not inhibit the desired properties of the sol of the present embodiment and its crosslinking effect is ensured. As the derivatives of genipin, for example, those described in JP 2006-500975 T can be used. The term "genipin" as used herein also means a polymer of genipin. It is known that genipin is polymerized under various conditions. Although no particular limitation is imposed on the polymerization conditions and method thereof, for example, a method of polymerizing it by aldol condensation under strong alkali conditions (Mi et al. Characterization of ring-opening polymerization of genipin and pH-dependent cross-linking reactions between chitosan and genipin. Journal of Polymer Science: Part A: Polymer Chemistry, Vol. 43, 1985-2000 (2005)) can be used.

EDC is one of water-soluble carbodiimides. A water-soluble carbodiimide can be used as a crosslinking agent irrespective of its kind. Of these, inexpensive and highly safe EDC is particularly preferred. Water-soluble carbodiimides may be used either alone or in combination of two or more. The EDC may be used either alone or may be mixed with NHS. The crosslinking reaction by EDC is known to be accelerated by mixing with NHS.

When the sol of the present embodiment contains genipin, the concentration of genipin can be set at 1800 mg/L or less, preferably from 40 mg/L to 1400 mg/L, for example, from 100 mg/L to 1000 mg/L from the viewpoint of keeping the fluidity of the sol until the sol reaches an affected site. Adjustment of the genipin concentration within the above-described range makes it possible to enhance the gel strength by crosslinking while keeping fluidity of the sol in a catheter.

The sol of the present embodiment may further contain various solvents and additives used for a conventional aqueous collagen solution. Examples of such solvents and additives include acids such as diluted hydrochloric acid, citric acid, and acetic acid.

These additives or solvents may be used either alone or in combination of two or more. The respective contents of the additive and the solvent in the sol are not particularly limited insofar as they fall within a range not impairing the desired properties of the sol of the present embodiment.

The sol of the present embodiment is useful in the minimally invasive treatment using a catheter such as endoscopic treatment or IVR treatment. It is particularly useful for closure of a through-hole generated in the tissue, ulcer protection or vascular embolization.

For example, in endoscopic treatments such as EMR (endoscopic mucosal resection) or ESD (endoscopic submucosal dissection), incidence of perforation as an accidental symptom has become a problem. The perforation is closed by clipping, but it takes time to deliver several clips one by one via a scope and an advanced operation technology of the endoscopic device is necessary for stable closure of the perforation. After-bleeding, delayed perforation, and so on due to unsatisfactory ulcer healing or the like after the endoscopic treatment have also been reported.

In IVR treatment, vascular embolization has been widespread. Vascular embolization is a technique of sending an embolic material into blood vessels through a catheter inserted in the artery in order to treat cancer such as liver cancer and stop bleeding from the digestive tract or lung. More specifically, it is a method of blocking the blood flow with an embolic material delivered to the vicinity of a lesion in the organ and then delivered respectively to the blood vessel which supplies a carcinomatous lesion with nutrition and to the blood vessel causing hemorrhage. A gelatin sponge conventionally used as an embolic material should be cut so as to fit the size of the affected part and an embolic material not fitting the size sometimes fails to achieve embolization. In addition to its problem, a coil is used as an embolic material but it is expensive and once it is delivered in the body, it remains therein permanently.

The sol of the present embodiment has such properties as a long fluidity retention time permitting delivery to the tissue through a catheter, body temperature response permitting gelation at the body temperature promptly after delivery, and adhesion to the tissue after gelation so that it is particularly useful in the above-described uses. More specifically, it is useful for the protection of an ulcer part (also repair of the ulcer part) formed during an endoscopic treatment such as ESD or EMR, closure of a perforation including temporary closure for facilitating a clipping operation, vascular embolization at the time of IVR treatment, and the like.

Conventional bio-adhesives have an increased viscosity promptly after preparation and after about one minute, they become a gel. The sol of the present embodiment, on the other hand, has a long fluidity retention time (for example, 10 minutes at room temperature) permitting delivery of it to the tissue through a catheter. Through a catheter having, for example, an inner diameter of 2.2 mm and a total length of 2.8 m, it can be delivered, for example, under an endoscope or a perspective image. In the present embodiment, delivery through a catheter includes delivery through a spray catheter. Although the inner diameter and length of a catheter to be used for delivery can be changed as needed, depending on an delivery site, viscosity of the sol, or the like, the catheter may have, for example, an inner diameter of from 0.5 mm to 2.8 mm and a length of from 1 m to 3 m. The sol of the present embodiment has such a property that it can be delivered to the tissue even if a catheter having a small inner diameter (for example, an inner diameter of from 0.5 mm to 2.5 mm) or a long catheter (for example, a length of from 1.5 m to 3 m) is used.

The viscosity of the sol of the present embodiment can be adjusted as needed, depending on the pore size of the catheter and for example, viscosity at 23° C. at a shear rate of 1 s$^{-1}$ is from 0.2 Pa·s to 52 Pa·s, preferably from 2 Pa·s to 20 Pa·s, more preferably from 5 Pa·s to 12 Pa·s. The sol having the viscosity within the above-described range can have fluidity during delivery and after delivery, it stays at an affected part and is formed into a gel at a desired position. Viscosity measurement can be performed, as shown later in Examples, based on a cone-plate system described in Japanese Industrial Standards (JIS) K7117-2 by using a known rheometer having a controllable shear rate. A polymer solution such as the collagen sol of the present embodiment is a non-Newtonian fluid and with an increase in the shear rate at the time of measurement, its viscosity decreases and converges into a certain viscosity value. Therefore, the viscosity of the sol of the present embodiment is described as a viscosity measured at a low shear rate at which a viscosity difference can be observed clearly, more specifically, at a shear rate of 1 s$^{-1}$.

The sol of the present embodiment, after being delivered to the tissue through a catheter as described above, starts gelation promptly at the temperature of the living body (body temperature) and locally becomes a gel, with which tissue perforation closure, ulcer protection, and vascular embolization can be performed. Gelation usually occurs within 5 minutes after the temperature reaches 37° C. after delivery. The strength of the gel thus formed is not particularly limited, but as a modulus of elasticity determined, for example, by a compression test or a penetration test described later in Examples, a range of from 10 kPa to 200 kPa is desired, with a range of from 20 kPa to 100 kPa being more preferred. Too small moduli of elasticity may lead to failure in tissue perforation closure or vascular embolization because the gel easily deforms. When the modulus of elasticity is much greater than that of the tissue around the gel, the strain of the tissue may cause failure in gel-tissue adhesion due to a difference in modulus of elasticity.

For locally forming a gel as described above, conversion of the collagen into fibrils (a kind of self-organization) occurs on the tissue to form a gel (primary gelation). When the sol contains a crosslinking agent such as genipin, a crosslink into the collagen fibril gel is introduced (secondary gelation), and the gel has enhanced strength and chemically bonds between the collagen and the tissue firmly.

The sol of the present embodiments can penetrate into the submucosal layer of the tissue and fix thereto.

The sol of the present embodiment having the above-described properties can form, locally and with good reproducibility in the living body where fluidity occurs, a gel having a fixing property to the tissue and strength both enough for closing a perforation or embolizing a blood vessel. The gel formed has a composition excellent in safety and biocompatibility and similar to the conventional collagen, it is gradually subjected to an action such as hydrolysis or enzymatic degradation.

The sol of the present embodiment may further contain a medicament, depending on the state of an affected part to be delivered. Although such a medicament is not particularly limited insofar as it can be incorporated in a conventional injectable gel, examples include medicaments such as physiologically active peptides, proteins, other antibiotics, anti-tumors, and hormone preparations. These medicaments may be used either alone or in combination of two or more. The content of the medicament is not particularly limited insofar as it is within the range that permits exhibition of efficacy of the medicament and does not hinder the desired properties of the gel of the present embodiment.

The present embodiment also relates to a kit for performing tissue perforation closure, ulcer protection, or vascular embolization with a sol which forms gel and attaches to the tissue when brought into contact with the tissue.

In one aspect, the kit includes a collagen for the formation of the sol, sodium chloride, and a buffer and it may further include genipin, a catheter for delivery of the sol, and the like if desired. The components constituting the kit may be in solution form. Alternatively, the sol may be formed by dissolving, as needed, the components incorporated in the kit in dry form before use.

In one aspect, the kit includes a tissue perforation closure sol containing from 0.6 mass % to 3 mass % of the collagen, water, from 200 mM to 330 mM sodium chloride, and a buffer and having a pH from 6.0 to 9.0; and genipin.

The present embodiment also relates to a tissue perforation closure method, an ulcer protection method, or a vascular embolization method, each using the above-described sol. Further, the present embodiment relates to a minimally invasive method such as endoscopic treatment or IVR treatment including any of the above-described methods. These methods can be performed referring to the above description relating to the sol of the present embodiment.

EXAMPLES

The present embodiment will hereinafter be described more specifically based on Examples and Comparative Examples, but the present invention is not limited to or by the following Examples and Comparative Examples.

[Preparation of Collagen Solution]

A solution of collagen obtained from porcine dermis having a concentration of 1.0 mass % (telopeptide-removed collagen, product of NH Foods, denaturation temperature of collagen: 40° C.) was prepared as a collagen stock solution. The collagen solution was concentrated using an evaporator (water-bath temperature: 29° C.) to obtain a collagen solution having a concentration of 2.4 mass %. The resulting solution was dispensed in 15-mL centrifuge tubes or 50-mL centrifuge tubes and stored in a refrigerator.

[Preparation of Aqueous Genipin Solution]

An aqueous genipin solution having a concentration of 24 mM (5430 mg/L) was prepared by dissolving genipin (product of Wako Pure Chemical) in pure water. The resulting aqueous solution was diluted with pure water to prepare aqueous genipin solutions different in concentration.

[Preparation of NPB]

An aqueous solution of disodium hydrogen phosphate having a concentration of 50 mM (containing 140 mM sodium chloride) and an aqueous solution of sodium dihydrogen phosphate having a concentration of 50 mM (containing 140 mM sodium chloride) were prepared using pure water as a solvent. The resulting solutions were stirred and mixed while measuring their pH by a pH meter ("NAVIh F-71", trade name; product of HORIBA) and a 50 mM phosphate buffer solution having a pH 7.0 and containing 140 mM sodium chloride was prepared. The buffer solution thus obtained was defined as 1×NPB. In all the Examples, the pH was measured using the above-described pH meter at 23° C. unless otherwise particularly specified. By a similar operation, 12×NPB (a 0.6 M phosphate buffer solution having a pH 7.0 and containing 1.68 M sodium chloride) was prepared. It was diluted with pure water into NPB (n×NPB) different in multiple.

Example 1

[a: Preparation of Collagen Sol: Used for Other than Animal Experiment]

The collagen solution (6 g) in the 15 mL centrifuge tube, prepared as described above, was allowed to stand in a polystyrene foam container filled with crushed ice. A magnetic stirrer (10.8 g, inner diameter: 10 mm×39 mm) for accelerating stirring was housed in the tube. Next, 2 mL of an aqueous genipin solution allowed to stand in a refrigerator of 4° C. and 2 mL of the 10×NPB allowed to stand at room temperature were sucked up with a micropipette, respectively, and added to the centrifuge tube containing the collagen solution. The centrifuge tube was stirred by vigorous shaking. After stirring for about 30 seconds, the centrifuge tube was set at a predetermined position of a centrifuge separator and centrifuge separation was performed under conditions of 3200 rpm and 1.5 minutes to collect air bubbles on the liquid upper surface and obtain 1.44% collagen sol (solvent: 2×NPB, genipin concentration: 4 mM (905 mg/L)).

[b: Preparation of Collagen Sol: Used for Animal Experiment]

The collagen solution (12 g) in the 50 mL centrifuge tube, prepared as described above, was allowed to stand in a polystyrene foam container filled with crushed ice. A magnetic stirrer (10.8 g, inner diameter: 10 mm×39 mm) for accelerating stirring was housed in the tube. Next, 4 mL of a 20 mM aqueous genipin solution allowed to stand in the container filled with crushed ice and 4 mL of the 10×NPB allowed to stand at room temperature were sucked up with a micropipette, respectively, and added to the centrifuge tube containing the collagen solution. The centrifuge tube was stirred by vigorous shaking to obtain 1.44% collagen sol (solvent: 2×NPB, genipin concentration: 4 mM (905 mg/L)). The resulting product was used for a in vivo experiments for closing tissue perforation of porcine stomachs of Example 1.

Example 2

A collagen sol having a composition similar to that of Example 1 except that the collagen concentration was increased from 1.44% to 1.6% was prepared.

Example 3

A collagen sol having a composition similar to that of Example 1 except that the NPB concentration was reduced from 2×NPB to 1.8×NPB was prepared.

Example 4

A collagen sol having a composition similar to that of Example 1 except that the NPB concentration was reduced from 2×NPB to 1.6×NPB was prepared.

Example 5

A collagen sol having a composition similar to that of Example 1 except that the genipin concentration was reduced from 4 mM to 2 mM (452 mg/L) was prepared.

Example 6

A collagen sol having a composition similar to that of Example 1 except that it did not contain genipin was prepared.

Comparative Example 1

A collagen sol similar to that of Example 1 except that the NPB concentration was increased from 2×NPB to 2.4×NPB and the genipin concentration was increased from 4 mM to 8 mM (1810 mg/L) was prepared.

Comparative Example 2

A collagen sol having a composition similar to that of Example 1 except that the NPB concentration was reduced from 2×NPB to 1×NPB was prepared.

Comparative Example 3

A collagen sol having a composition similar to that of Example 1 except that the NPB concentration was reduced from 2×NPB to 1×NPB and the collagen concentration was reduced from 1.44% to 0.5% was prepared.

[Test Method]

[In Vivo Experiments for Closing Tissue Perforation of Porcine Stomachs]

An acute perforation closure experiment was performed using an SPF pig (weight: 30 kg). Under general anesthesia, a virtual lesion obtained by locally injecting saline into the submucosa of the porcine stomach to create a mucosal elevation, was subjected to ESD with a knife exclusively used for ESD. A perforation having an inner diameter of 5 mm was formed at the ulcer floor thus obtained. After confirmation of the collapse of the stomach due to deaeration, the collagen sol was delivered promptly to the perforated portion via a catheter (total length: 2400 mm, "Fine Jet S2825", trade name; product of Top, inner diameter: 2.2 mm; cut at 100 mm from its tip end with scissors). After confirmation of the dilation of the stomach by air supply, the pig was rested for one hour. The pig was then euthanatized and the stomach was resected therefrom. A leak test was performed by closing the pyloric portion of the stomach with a forceps and injecting water from the cardia to fill the stomach with water. After the leak test, a site including the perforated portion was resected and fixed and then provided for the histological observation by hematoxylin-eosin (HE) staining.

[In Vivo Experiments for Closing Tissue Perforation of Porcine Colons]

An acute perforation closure experiment was performed using an SPF pig (weight: 30 kg). Under general anesthesia, a perforation having an inner diameter of 5 mm was formed in the porcine colon with a knife exclusively used for ESD. Promptly after confirmation of the collapse of the colon due to deaeration, the collagen sol was delivered to the perforated portion via a catheter (similar to that used in the [in vivo experiments for closing tissue perforation of porcine stomachs]). After confirmation of the dilation of the colon due to air supply, the pig was rested for one hour. The pig was euthanatized and the colon was cut and resected therefrom. A leak test was then performed by closing the resulting colon at one side thereof with a forceps and injecting water from the opening on the other side to fill the colon with water.

[Ex Vivo Ulcer Protection Test Using Porcine Stomach]

An ex vivo ulcer protection test using the porcine resected stomach was performed by imitating the covering treatment, with a collagen sol, of an ulcer caused by endoscopic treatment. Saline was locally injected into the submucosa of the porcine resected stomach having a size of about 60×60 mm via a 23G needle to create a mucosal elevation and a 30×30 mm artificial ulcer was formed at the center of the resected stomach with a surgical scalpel. The specimen thus prepared was fixed on an aluminum plate inclined at 60° and placed in an incubator ("Rcom Max 20", product of Autoelex) set at 37° C. and humidity of 70%. After confirmation that the surface temperature of the specimen reached 37° C. by using an infrared thermometer ("IT-545", product of HORIBA), the collagen sol (3 mL) was delivered to the artificial ulcer portion of the specimen via a 18G syringe needle. The collagen sol was allowed to stand for 2 hours as it is to complete gelation of the collagen.

To evaluate the adhesion and thickness of the collagen gel formed at the artificial ulcer portion, the specimen was provided for histological observation. The specimen was fixed with a 4% aqueous paraformaldehyde solution. After substitution with a 20% aqueous sucrose solution, the specimen was embedded with a 4% aqueous carboxymethyl cellulose solution. After freezing at −100° C. for 5 minutes, a 20 μm thick section was prepared using a frozen microtome ("CM3050S", product of Leica microsystems). The section thus obtained was air-dried, followed by hematoxylin-eosin staining. After washing with an aqueous ethanol solution having a concentration gradually increased from 70% to 99.5% and covering with a mounting medium ("Eukitt", product of Kindler), the section was observed under an upright microscope ("BX53", product of Olympus).

[Dynamic Viscoelasticity Test]
[Viscosity Measurement]

The viscosity of the collagen sol was measured in a rotation mode using a dynamic viscoelasticity measuring apparatus ("HAAKE MARS III" product of Thermo Fisher Scientific). A double cone sensor ("DC60/1Ti", cone angle: 1°) set at 23° C. and having an inner diameter of 60 mm was filled with the collagen sol and rotation at a shear rate of 1 $s^{-1}$ was started. The shear rate was increased to 100 $s^{-1}$ step by step while setting the retention time of each step at 20 seconds and a stress was measured. From the shear rate and the stress, a viscosity was calculated. After confirmation from the viscosity curve thus obtained (viscosity vs shear rate) that the collagen sol had non-Newtonian flow characteristics, the viscosity value at the shear rate at 1 $s^{-1}$ was used.

[Measurement of Dynamic Viscoelasticity]

A gelation rate of the collagen sol responsive to the body temperature was measured by dynamic measurement (oscillation mode) using a dynamic viscoelasticity measurement apparatus (similar to that used for the viscosity measurement). A double cone sensor set at 23° C. was filled with the collagen sol and dynamic measurement (frequency: 1 Hz, shear strain: 0.005) was started while controlling the shear strain. After 5 minutes, the temperature was increased from 23° C. to 37° C. in 30 s and the temperature was kept at 37° C. as is. Throughout the above procedure, a change in each of a storage modulus (G') and a loss modulus (G") was traced. A period of time during which the viscoelasticity properties changed from G'<G" at room temperature to G'=G" after the apparatus temperature reached 37° C. was defined as a gelation time.

[Penetration Test of Gel Formed on Dish]

The dynamic properties of the collagen gel were evaluated by causing a probe to penetrate into the center portion of the gel and thereby carrying out a mechanical test. About 3 g/well (inner diameter: 35 mm) of the collagen sol was added to a 6-well biological plate and the plate was heated by floating it in a water bath of 37° C. After 30 minutes, the entire plate was covered with a Parafilm to prevent it from drying and allowed to stand for 24 hours in an incubator of 37° C. to complete gelation. A columnar probe made of stainless having a diameter of 5 mm was caused to penetrate into the center portion of the resulting gel at a rate of 0.2 mm/s by a texture analyzer ("TA. XTplus", product of Stable Microsystems) and a stress-strain curve was obtained. The modulus of elasticity of the gel was calculated from the gradient of a linear region of the stress-strain curve at a strain of from 0.005 to 0.04.

[Test 1]

The in vivo experiments for closing tissue perforation of porcine stomachs described in the test method was performed using the collagen sol of Example 1. FIG. 1 shows how a perforation was formed in the porcine stomach, a collagen sol was delivered, gelation occurred, and the perforation was closed. The closure of the perforated portion was proved by the dilation of the stomach caused by air supply immediately after gelation of the sol in the perforated portion.

Figure 2:
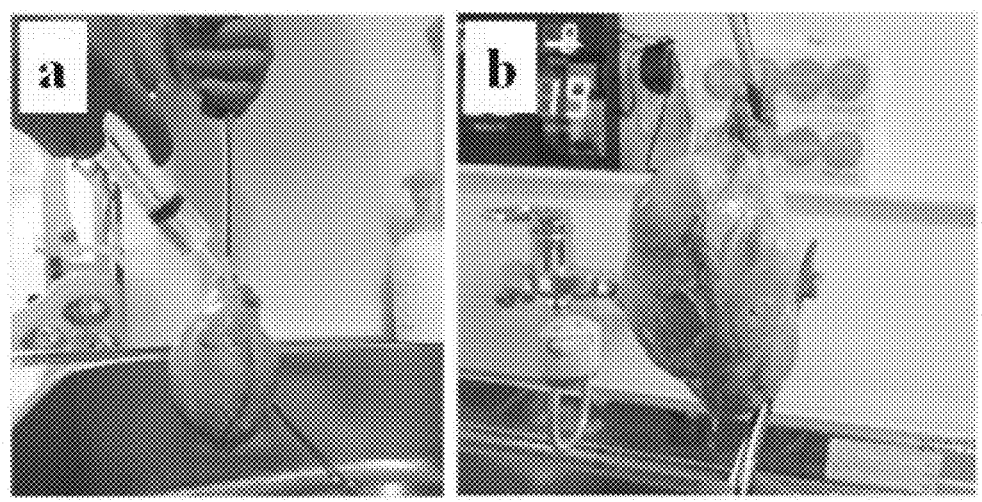
FIG. 2 shows a leak test from the resected stomach in the in vivo experiments for closing tissue perforation of porcine stomachs in Test 1.

FIG. 2 shows how a leak test of the resected stomach was performed. No water leakage was observed from two closed perforations, proving that closure of the perforated portions was maintained.

Figure 3:
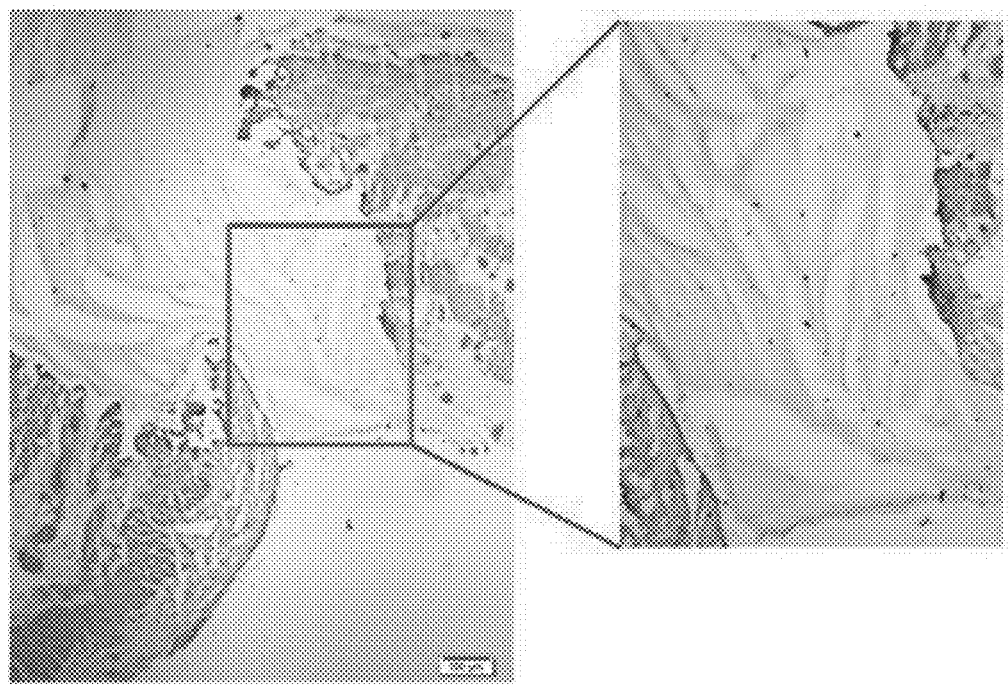
FIG. 3 shows a HE stained image of the porcine stomach tissue including a perforated portion in the in vivo experiments for closing tissue perforation of porcine stomachs in Test 1.

FIG. 3 shows an HE stained image of the porcine stomach tissue including the perforated portion. The perforated portion was closed as if it was stoppered with the gel and close adhesion between the gel and the tissue was observed.

[Test 2]

Figure 4:
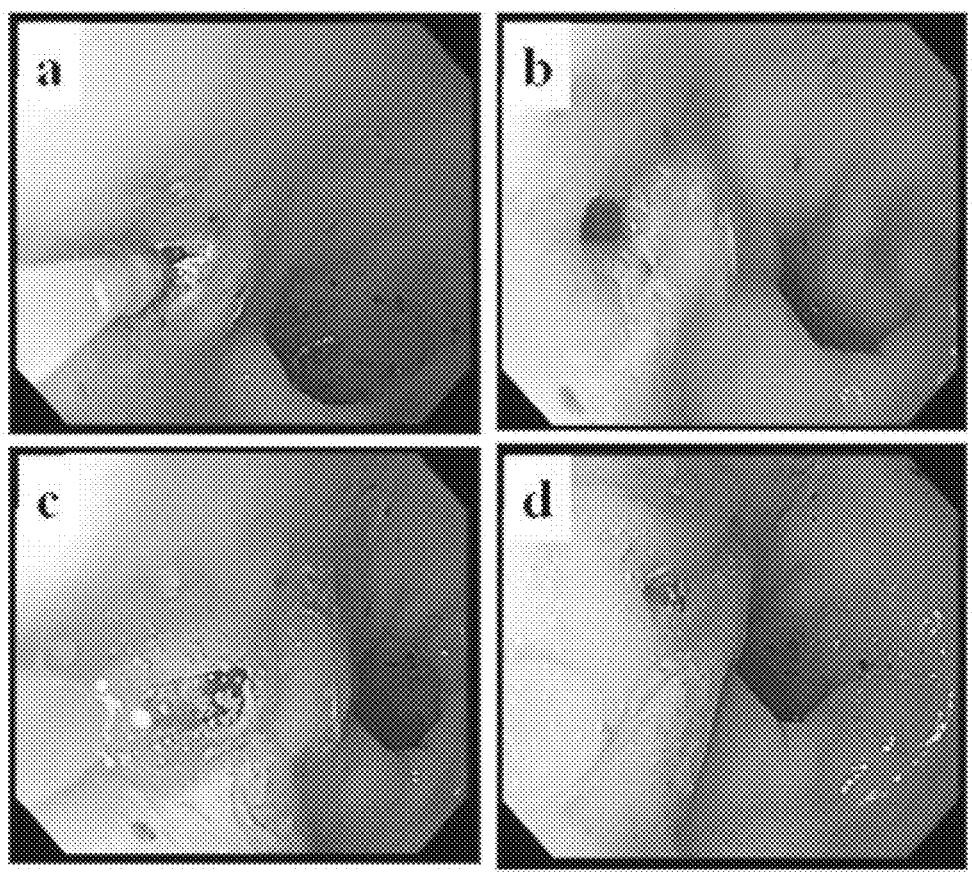
FIG. 4 shows, in in vivo experiments for closing tissue perforation of porcine colons in Test 2, perforation in a porcine colon (FIG. 4a), delivery of a collagen sol (FIG. 4b), gelation (FIG. 4c), and perforation closure (FIG. 4d).

The in vivo experiments for closing tissue perforation of porcine colons described in the test method was performed using the collagen sols obtained in Examples 1 and 2. FIG. 4 shows how a perforation was formed in the porcine colon, a collagen sol was delivered, and the perforation was closed. The closure of the perforated portion was proved by the dilation of the colon caused by air supply immediately after gelation of the sol in the perforated portion.

Figure 5:
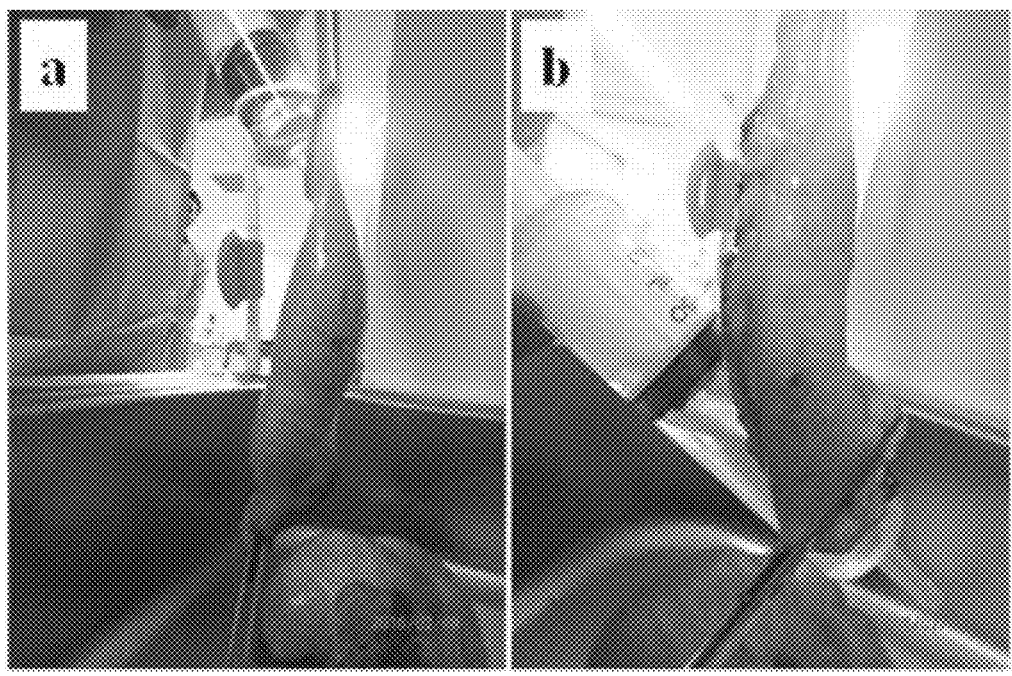
FIG. 5 shows a leak test from the resected colon in the in vivo experiments for closing tissue perforation of porcine colons in Test 2.

FIG. 5 shows a leak test of the resected colon. No water leakage was observed from two closed perforations when using either of the collagen sols, proving that the closure of the perforated portions was maintained. When the collagen sol of Example 1 was used for the color perforation closure, the sol sometimes flew out from the colon due to a pressure difference at the perforated portions and failed to form a gel at the perforated portions. Using the collagen sol of Example 2 having a concentration (1.6%) higher than that (1.44%) of the collagen sol of Example 1, on the other hand, facilitated gel formation at the perforated portions.

[Test 3]

Figure 6:
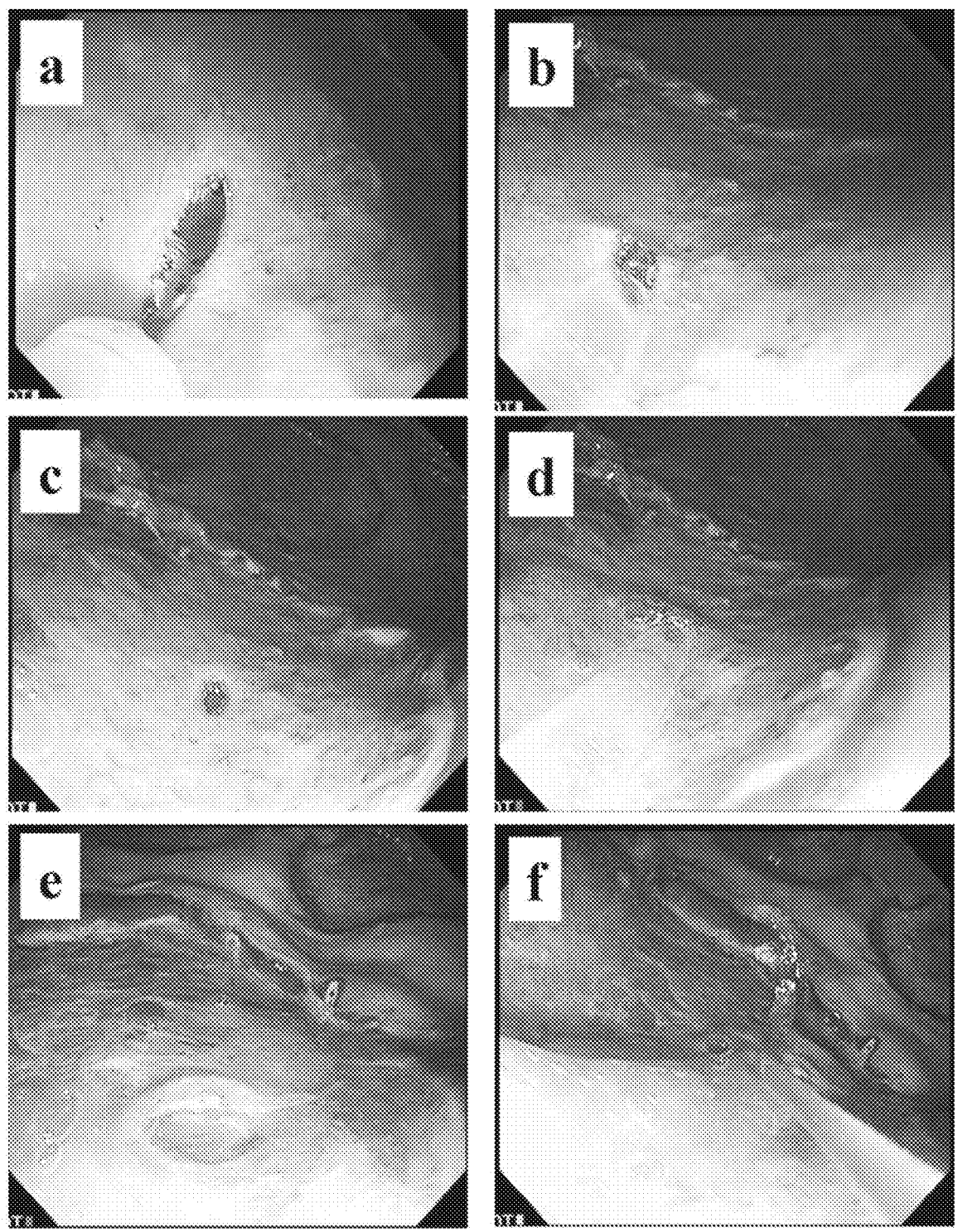
FIG. 6 shows, in in vivo experiments for closing tissue perforation of porcine stomachs in Test 3, perforation in a porcine stomach (FIG. 6a), delivery of a collagen sol (FIG. 6b), gelation (FIG. 6c), perforation closure (FIG. 6d), closure of a large perforation (FIG. 6e), and the gel not broken even by saline jetted thereto (FIG. 6f).

The in vivo experiments for closing tissue perforation of porcine stomachs described in the test method was performed using the collagen sol of Example 3. FIG. 6 shows how a perforation was formed in the ulcer floor of the porcine stomach prepared in a manner similar to that of Test 1, a collagen sol was delivered, and the perforation was closed. The closure of the perforated portion was proved by the dilation of the stomach caused by air supply immediately after gelation of the sol in the perforated portion. The gel was not broken even by saline jetted thereto (FIG. 6).

A perforation having a larger inner diameter (inner diameter: 10 mm) was made at another position and was closed with the gel similarly (FIG. 6e). The gel was not broken even by saline jetted thereto (FIG. 6f). The gel that had spread and attached to the ulcer floor around the perforation was not detached by saline jetted thereto and protection of the ulcer with the gel was confirmed. The collagen sol of Example 3 contained genipin at a concentration similar to that of Examples 1 and 2 so that it was considered that the strength at the time of gelation was sufficient for ulcer protection.

[Test 4]

Figure 7:
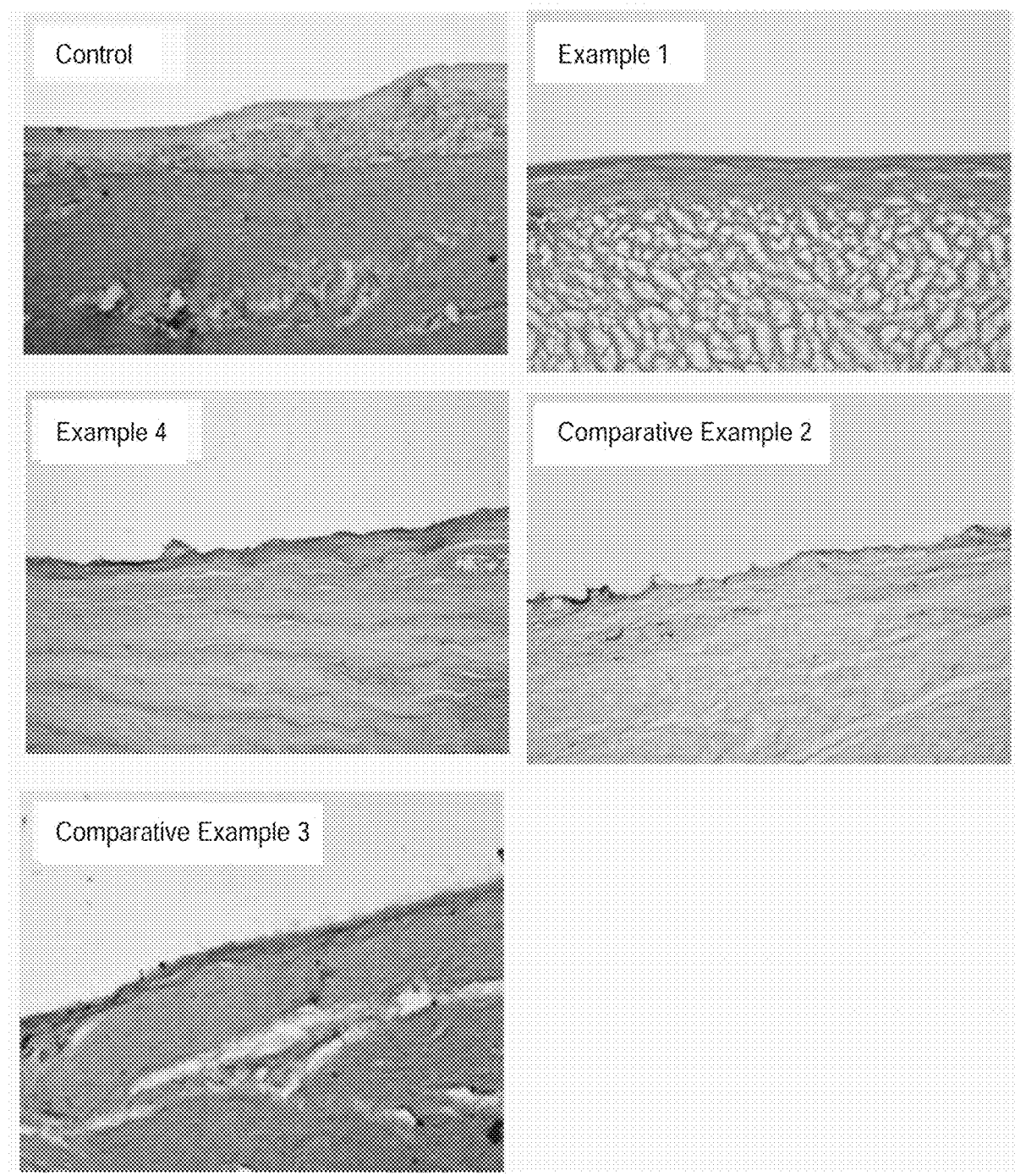
FIG. 7 shows the results of an ex vivo ulcer protection test of the porcine stomach in Test 4.

The ex vivo ulcer protection test of the porcine stomach described in the test method was performed using the respective collagen sols of Example 1, Example 4, Comparative Example 2, and Comparative Example 3. The results are shown in FIG. 7. When the respective collagen sols of Example 1 and Example 4 were each sprayed to an inclined ulcer portion of the resected porcine stomach, formation of a collagen gel layer similar to that in a control test was found on the surface of the submucosal layer. As a result of measurement, the thickness of the gel layer was 24±4 mm (average value±standard deviation of 10 layers) when the sol of Example 1 was used, while it was 20±2 mm (average value±standard deviation of 10 layers) when the sol of Example 4 was used.

The ulcer portion is not always positioned on the lower side of the stomach in the actual surgery. If it is positioned on the lower side, the sol forms a gel without dissipating from the ulcer floor even if there is time for the sol to form a gel (Control shown in FIG. 7). But, in clinical practice, the ulcer portion is often positioned on the lateral side of the stomach. The results of the present test show that the sol of Examples promptly forms a gel and the gel layer thus obtained can protect even the lateral-side ulcer where the sol may easily dissipate due to the gravity.

When the collagen sol of Comparative Example 2 was used, on the other hand, there appeared a site with a collagen gel layer and a site without it. Even at the gel-layer formed site, the thickness of the gel layer decreased even to 11±2 mm (average value±standard deviation of 10 gel layers). It was considered that because a decrease in NPB concentration caused a decrease in the concentration of sodium chloride contained in the sol even to 140 mM, which was equal to the concentration of PBS, and deterioration in response of collagen fibril formation to body temperature (refer to Test 5 and FIG. 8) occurred, almost all the sprayed collagen sol inevitably dissipated from the ulcer portion before gelation.

When the collagen sol of Comparative Example 3 was used and it was sprayed to the inclined ulcer portion of the porcine resected stomach, the collagen sol dissipated from the ulcer portion before gelation and formation of the gel layer was not found from the histological section. It was considered that the decrease in the collagen concentration made it difficult to protect the ulcer with the gel.

[Test 5]

The dynamic viscoelasticity test of the respective collagen sols of Example 1, Example 2, and Comparative Example 2 was performed. FIG. 8a shows the evaluation results of the response of gelation to the body temperature.

When the respective collagen sols of Example 1 and Example 2 were used, the G' did not a change for the first 5 minutes during which the apparatus temperature was maintained at 23° C. Immediately after the temperature reached 37° C., G' showed an exponential increase.

When the collagen sol of Comparative Example 2 was used, response of collagen fibril formation to the body temperature deteriorated, presumably because due to the decrease in NPB concentration, the concentration of sodium chloride contained in the sol decreased even to 140 mM which is equal to that of PBS.

Next, the dynamic viscoelasticity test of the respective collagen sols of Example 1, Example 5, and Example 6 (genipin concentrations: 4 mM, 2 mM, and 0 mM, respectively) was performed. FIG. 8b shows the results of tracing the G' for 30 minutes after the measurement was started (24.5 minutes after the apparatus temperature reached 37° C.). A difference in the concentration of genipin had almost no influence on an exponential increase of G' immediately after the apparatus temperature reached 37° C., but G' gradually increased depending on the concentration of genipin after 5 minutes after the apparatus temperature reached 37° C. When genipin was not added, on the other hand, an increase in G' almost stopped 7 minutes after the apparatus temperature reached 37° C.

Figure 8:
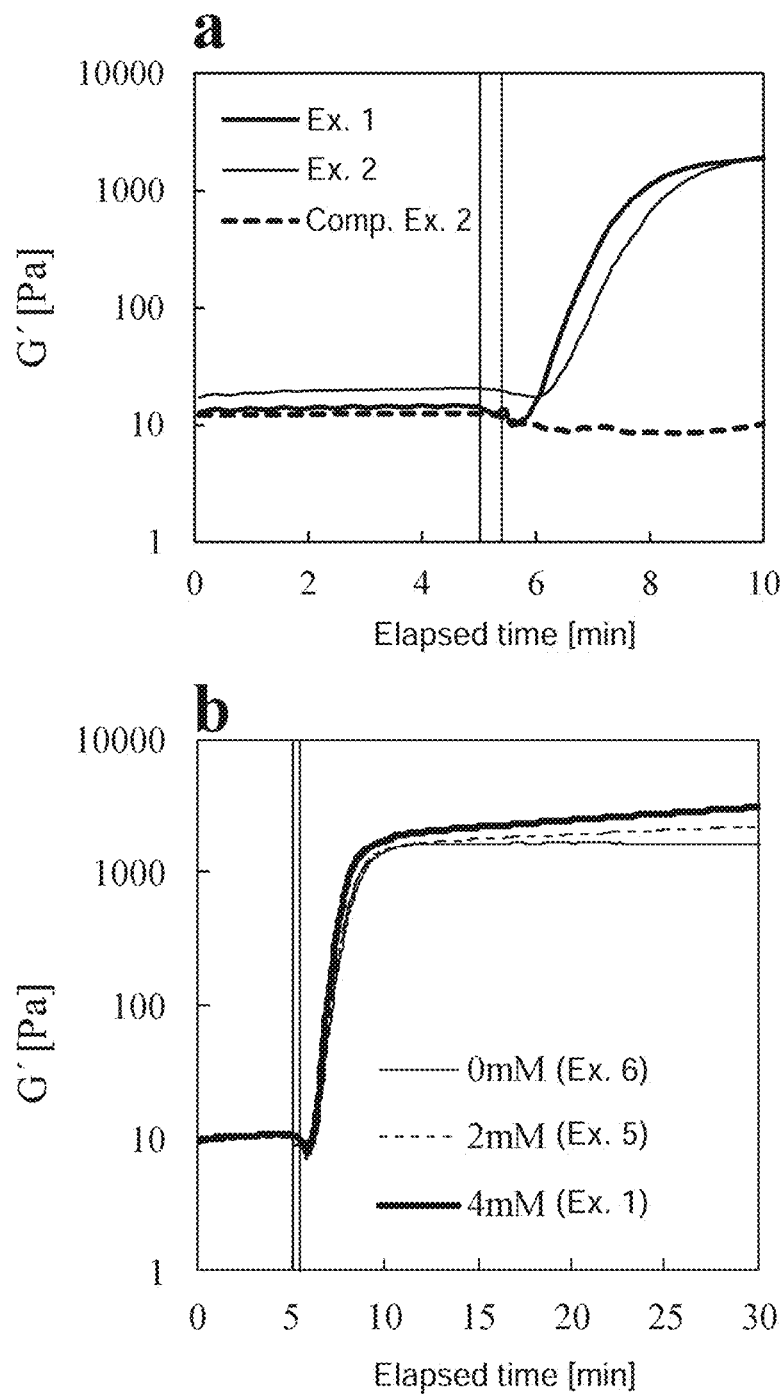
FIG. 8 shows the results of a dynamic viscoelasticity test of a collagen sol in Test 5.

The results shown in FIG. 8 have suggested that a firm gel can be obtained by a two-stage step, that is, gelation of a collagen sol due to collagen fibril formation promptly after being brought into contact with the tissue and gradual crosslinking of the resulting collagen fibril gel by genipin.

[Test 6]

Figure 9:
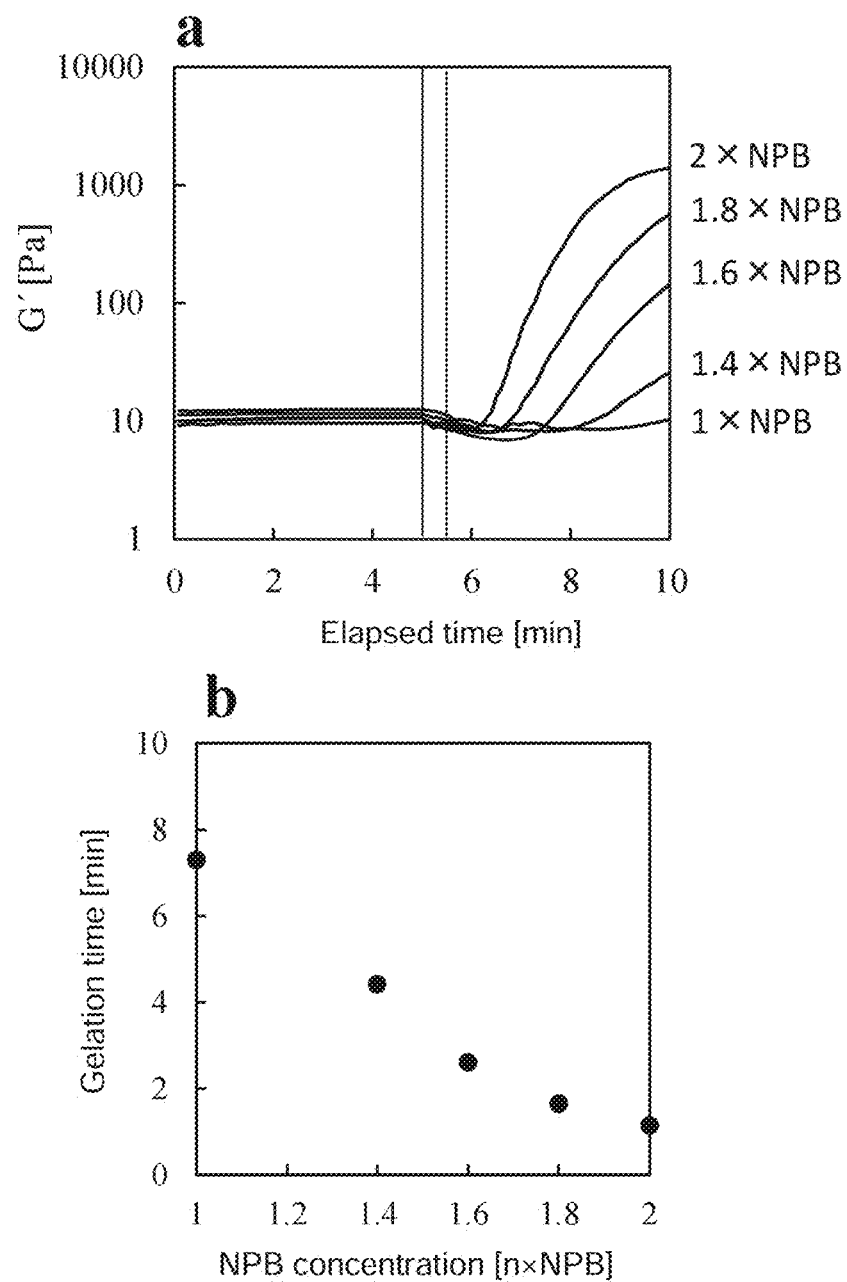
FIG. 9 shows the results of a dynamic viscoelasticity test of a collagen sol in Test 6.

To describe gelation by collagen fibril formation separately from gelation by genipin crosslinking, a dynamic viscoelasticity test was performed by changing the NPB concentration (2×NPB) of the collagen sol of Example 6, that is, a genipin-free 1.44% collagen sol, to 1, 1.4, 1.6, and 1.8 (×NPB) and the gelation behavior due to fibril formation responsive to the body temperature was studied. The results are shown in FIG. 9a. When 1×NPB corresponding to PBS generally used as an isotonic solution was used, an increase in G' was not observed for about 5 minutes after the apparatus temperature reached 37° C., showing slow collagen fibril formation. When the NPB concentration was increased, on the other hand, gelation responsive to the body temperature was accelerated, depending on the NPB concentration. Also the results (FIG. 9b) of plotting the gelation time after the temperature reached 37° C. with respect to the NPB concentration have revealed that the gelation by the collagen fibril formation was accelerated by the increase in NPB concentration.

[Test 7]

Figure 10:
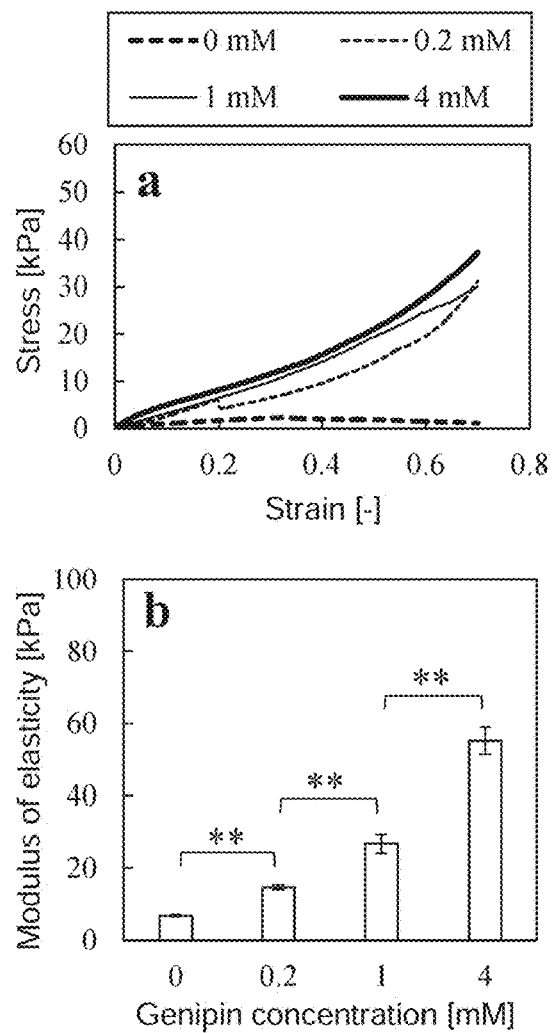
FIG. 10 shows the results of a penetration test of gels in Test 7.

FIG. 10 shows the results of a penetration test of gels formed on dishes by using the collagen sols of Example 1 and Example 6 (respectively having a genipin concentration of 4 mM and 0 mM), and collagen sols obtained by changing the genipin concentration of the above-described sols to 0.2 mM and 1 mM, respectively. An entire gradient of the stress-strain curve thus obtained increased with the genipin concentration, showing that the collagen gels had improved strength by the addition of genipin. An increase in the gradient almost stopped from the genipin concentration of from 1 mM to 4 mM (concentration of Example 1) (FIG. 10a). The gel obtained without addition of genipin was weak and brittle.

On the other hand, the modulus of elasticity of the collagen gel increased with the genipin concentration, but the increase until 4 mM was monotonous (FIG. 10b). The modulus of elasticity of the gel (having a genipin concentration of 4 mM) derived from the sol of Example 1 was about 8 times higher than that of the gel derived from the genipin-free sol of Example 6.

The results of FIG. 10 have revealed that the gel obtained using the sol having a genipin concentration of 1 mM had a gel strength similar to that of the gel of Example 1 obtained using the sol having a genipin concentration of 4 mM and had a modulus of elasticity 4.0 times higher than that of the genipin-free gel. This suggests that addition of genipin makes it possible to form, in the perforated portion, a gel harder than that derived from a genipin-free collagen sol.

[Test 8]

Figure 11:
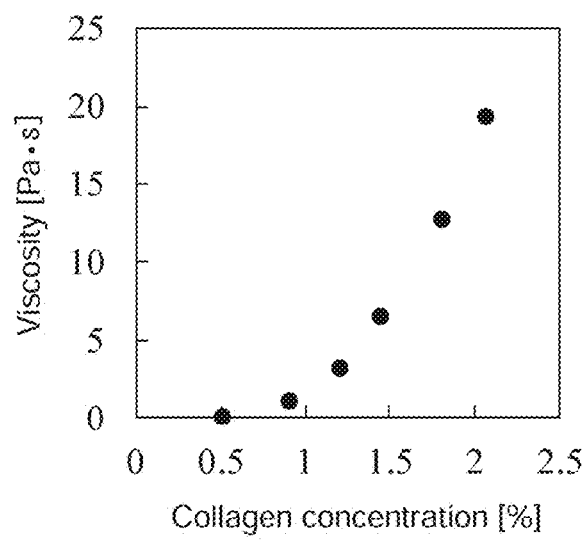
FIG. 11 shows the measurement results of a viscosity in Test 8.

FIG. 11 shows the measurement results, at a shear rate of 1 $s^{-1}$ in a rotation mode of the dynamic viscoelasticity measuring apparatus, of the viscosities of sols obtained by changing the collagen concentration of the collagen sol of Example 6 (having a collagen concentration of 1.44%) to 0.5, 0.9, 1.2, 1.8, and 2.06%, respectively.

The viscosity was only 0.12 (Pa·s) when the collagen concentration was 0.5%. At the concentration increased to 1.44%, the viscosity increased to 6.56 (Pa·s) and at the concentration increased to 2.06%, the viscosity reached 19.4 (Pa·s). Since the viscosity of the collagen sol shows an exponential change with respect to the collagen concentration, it is important to adjust the concentration to satisfy two contradictory properties, that is, local retention of the collagen sol in the digestive tract and an introduction property of it through a thin tube such as a catheter.

[Test 9]

Figure 12:
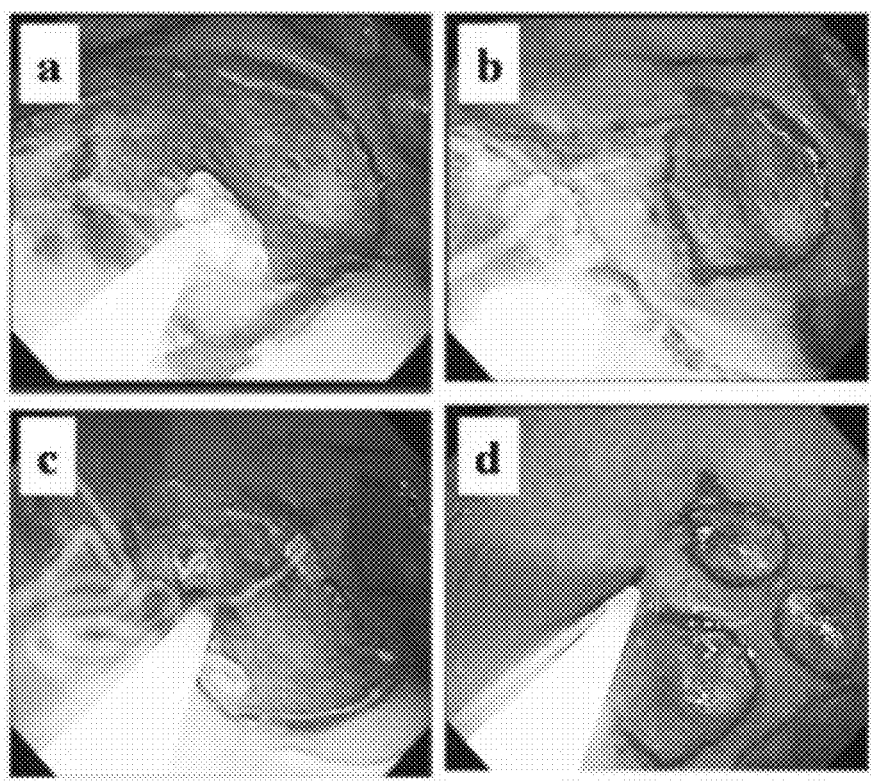
FIG. 12 shows the results of in vivo experiments for closing tissue perforation of porcine stomachs using a collagen sol of Comparative Example 1 in Test 9.

A in vivo experiments for closing tissue perforation of porcine stomachs was performed using the collagen sol of Comparative Example 1. As shown in FIG. 12, however, the sol discharged from the catheter had already formed gel (FIG. 12a) and the collagen which formed gel in a string form slid down without adhering to the ulcer floor (FIG. 12b). In spite of discharging another portion of the sol, a string-like collagen gel was discharged from the tip of the catheter (FIG. 12c and FIG. 12d).

An endoscope placed to pass the oral cavity and esophagus is warmed by the body temperature and a catheter inserted therein is also warmed to a temperature higher than the room temperature. A collagen sol containing high concentrations of NPB and genipin and therefore excessively accelerated in body-temperature-responsive gelation sometimes forms gel before delivered to an affected portion, so that it is considered unsuitable for uses such as tissue perforation closure, ulcer protection, and vascular embolization.

TABLE 1

PH and composition of collagen sols and evaluations performed

| | | Composition of collagen sol | | | |
|---|---|---|---|---|---|
| | pH | Collagen (%) | Genipin (mM) | NPB (n × NPB) | Sodium chloride (mM) | Evaluation * |
| Ex. 1 | 7.0 | 1.44 | 4 | 2 | 280 | A, C, D, E |
| Ex. 2 | 7.0 | 1.6 | 4 | 2 | 280 | B, D, F |
| Ex. 3 | 7.0 | 1.44 | 4 | 1.8 | 252 | A |
| Ex. 4 | 7.0 | 1.44 | 4 | 1.6 | 224 | C |
| Ex. 5 | 7.0 | 1.44 | 2 | 2 | 280 | D |
| Ex. 6 | 7.0 | 1.44 | 0 | 2 | 280 | D |
| Comp. Ex. 1 | 7.0 | 1.44 | 8 | 2.4 | 336 | A |
| Comp. Ex. 2 | 7.0 | 1.44 | 4 | 1 | 140 | C, D |
| Comp. Ex. 3 | 7.0 | 0.5 | 4 | 1 | 140 | C |

* Evaluation
A: Closing tissue perforation in porcine stomachs in vivo
B: Closing tissue perforation in porcine colons in vivo
C: Ex vivo ulcer protection of porcine stomach
D: Evaluation of response of gelation to body temperature
E: Penetration test of gel
F: Rotational viscosity measurement

INDUSTRIAL APPLICABILITY

The sol of the present invention is equipped with the following three properties suited for through-hole closure, physical protection of ulcer, and vascular embolization: (1) long fluidity retention time permitting delivery to the living body, from outside to inside, through a catheter, (2) a sharp response to the body temperature to form gel promptly after delivery, and (3) a property of curing after gelation and fixing to the tissue so that it can achieve through-hole closure, physical protection of ulcer, and vascular embolization. The present invention has industrial applicability in medical fields.

The present application claims priority to Japanese Patent Application No. 2016-224255 filed on Nov. 17, 2016 and the entire content of it is hereby incorporated by reference.

What is claimed is:

1. A method of treating a perforation in a tissue, protecting a tissue against ulceration, embolizing vasculature in a tissue, or adhering a tissue with a gel having a modulus of elasticity of 10 kPa to 200 kPa, which comprises forming the gel on or in the tissue via a two-stage cross-linking process by delivering to the tissue a sol comprising from 1.4 mass % to 1.6 mass % of a collagen, water, 252 mM sodium chloride, at least 0.2 mM genipin, and a buffer and having a pH from 6.0 to 9.0, wherein the buffer contains a phosphate and the collagen includes a telopeptide-removed collagen.

2. The method of claim 1, wherein the tissue has a perforation and the sol is applied thereto.

3. The method of claim 1, wherein the tissue has an ulcer and the sol is applied thereto.

4. The method of claim 1, wherein the tissue is protected against ulceration by application of the sol.

5. The method of claim 1, wherein the vasculature of the tissue is embolized upon delivery of the sol.

6. The method of claim 1, wherein the sol adheres parts of the tissue together.

7. The method according to claim 1, wherein the sol comprises from 0.2 mM to 4 mM of genipin.

8. The method according to claim 1, wherein the sol is locally delivered to the tissue through a catheter.

9. The method according to claim 1, wherein said sol forms the gel, wherein the gel attaches to the tissue when contacted therewith.

10. The method of claim 1, wherein the modulus of elasticity is 20 kPa to 100 kPa and the concentration of genipin is 100 mg/L to 1000 mg/L.

11. A method of treating a perforation in a tissue, protecting a tissue against ulceration, embolizing vasculature in a tissue, or adhering a tissue with a gel having a stress-strain profile whereby the amount of stress increases with the amount of strain, which comprises forming the gel on or in the tissue via a two-stage cross-linking process by delivering to the tissue a sol comprising from 1.4 mass % to 1.6 mass % of a collagen, water, 252 mM sodium chloride, at least 0.2 mM genipin, and a buffer and having a pH from 6.0 to 9.0, wherein the buffer contains a phosphate and the collagen includes a telopeptide-removed collagen.

12. The method of claim 11, wherein the tissue has a perforation and the sol is applied thereto.

13. The method of claim 11, wherein the tissue has an ulcer and the sol is applied thereto.

14. The method of claim 11, wherein the tissue is protected against ulceration by application of the sol.

15. The method of claim 11, wherein the vasculature of the tissue is embolized upon delivery of the sol.

16. The method of claim 11, wherein the sol adheres parts of the tissue together.

17. The method according to claim 11, wherein the sol is locally delivered to the tissue through a catheter.

18. The method according to claim 11, wherein said sol forms the gel, wherein the gel attaches to the tissue when contacted therewith.

19. The method according to claim 11, wherein said sol has a viscosity from 0.2 Pa·s to 52 Pa·s at 23° C. and a shear rate of 1 $s^{-1}$.

20. A method of treating a perforation in a tissue, protecting a tissue against ulceration, embolizing vasculature in a tissue, or adhering a tissue with a gel having a modulus of elasticity of 20 kPa to 100 kPa, which comprises delivering to the tissue a sol comprising from 1.4 mass % to 1.6 mass % of a collagen, water, 252 mM sodium chloride, 100 mg/L to 1000 mg/L genipin, and a buffer and having a pH from 6.0 to 9.0, wherein the buffer contains a phosphate and the collagen includes a telopeptide-removed collagen.

* * * * *